US00PP07766P

United States Patent [19]

Rawdon

[11] Patent Number: Plant 7,766

[45] Date of Patent: Jan. 14, 1992

[54] GREY DOGWOOD 'CINDERELLA'

[76] Inventor: Alanson T. Rawdon, P.O. Box 227, Holt, Mo. 64048

[21] Appl. No.: 587,341

[22] Filed: Sep. 24, 1990

[51] Int. Cl.[5] ..... A01H 5/00
[52] U.S. Cl. ..... Plt./51
[58] Field of Search ..... Plt./51

*Primary Examiner*—James R. Feyrer

[57] ABSTRACT

There is disclosed a new and distinct variety of Grey Dogwood botanically known as *Cornus racemosa.* The new variety possesses attractive variegated leaves wherein the central portion is medium green and the margin is yellow fading to cream as the leaf matures.

1 Drawing Sheet

BACKGROUND AND SUMMARY OF THE NEW PLANT

The variety originated as a branch 'sport' of a variegated Grey Dogwood found by our family while clearing some woods near our home. This weakly growing plant was protected for one growing season and then yielded one scion that was successfully grafted in the spring of 1980. The graft was named *Cornus racemosa* 'Heaven Sent' and was outplanted in our nursery during the spring of 1983. The plant grew vigorously but failed to yield stable leaf variegations. In 1986 a single stem began to yield consistent leaf variegations of exceptional color and intensity. This stem has been isolated and asexually propagated for three seasons in a row using a side veneer graft and there has not been any signs of reverting or instability and given the name 'Cinderella'. The graft(s) have been vigorous and easy to grow.

This variety will enliven even the dullest of landscapes with its bright leaf variegations. The leaf color intensifies throughout the summer and by August it is the brightest plant in our landscape; whether growing in sun or shade. This cannot be said of the *Cornus florida* or *Cornus kousa* variegated selections. Their colors fade and scorch as the summer wears on; especially in full sun situations.

As fall approaches the new variety yields a mixed pattern of reds and yellows within the leaf which deepen with cooler weather. The reddish/pink inflorescences, usually stripped of berries by this time, is colorfully set off against the leaf background.

The white flowers and fruit, typical of the species, are borne in abundance and enhance the plant's overall ornamental value. For bird lovers, *Cornus racemosa* is a host to over 100 birds favoring the fruits. The winter reveals a distinct gray bark, typical of the species, and a clean plant effect. The plant can be expected to mature around 15 feet in height and spread. Blooming dates, and character of the fruit are substantially identical to those of the parent variety and of the species, but fruiting has been slightly heavier than that of the species.

With this introduction also comes a breakthrough in hardiness that extends into all areas of the United States. The plant has tremendous soil adaptability, surviving in all but the worst growing conditions. It is at home in sun or shade and colors well in both situations. Insects or disease have never been a problem regardless of growing condition.

DESCRIPTION OF THE DRAWING

The accompanying photographic drawing illustrates the new variety leaf variegations. The color being as nearly true as possible with color illustrations of this type.

DESCRIPTION OF THE NEW PLANT

The following detailed description sets forth the characteristics of the new variety. Color references are primarily to Munsells Book of Color.

CLASSIFICATION

This plant is a member of *Cornus racemosa,* commonly known as Grey Dogwood, which naturally occurs over a wide range in the central portion of the United States. The instant plant, denominated 'Cinderella', may be used as an appointment plant for landscape purposes to provide a splash of color in spring, summer and fall due to the interesting and novel coloration of its leaves.

PARENTAGE

The claimed plant is a stable limb sport of the variety 'Heaven Sent', the only other known commercial variety to the applicant. 'Cinderella' differs from 'Heaven Sent' in that it is faithfully stable while 'Heaven Sent' cannot be reliably asexually reproduced to produce identical specimens, even though these two plants may share the trait of leaf variegation.

GROWTH HABIT

'Cinderella' will mature to a shrub attaining a height and width of about 15 feet, and may be grown in the open or under shade. It is similar to the species in form and size, being basally dominant, and will spread when on its own stock. The plant will form a central leader when trained to do so, particularly when grafted on a seedling of the species. The plant is moderate to heavily branched, having branch crotch angles of about 60 degrees, as characteristic of the species. While having less chlorophyll due to its leaf variegation, 'Cinderella' is surprisingly vigorous, having a growth rate at least that of the species as demonstrated by specimens of comparable ages. Scions on seedling stocks show a growth rate of 8 to 12 inches per year, or more, which decreases with progressive years from graft placement. Internode lengths of 'Cinderella' do not substantially differ from those of the species; leaves are generally presented in whorls at stem terminals giving a full, balanced appearance for the plant, particularly when grown in the open.

INFLORESCENCE

Buds and flowers are representative of those of the species. Bracts which are typical of the species per se are presented in June with those of the species, and are retained in the same manner. While flower parts of this plant are no more conspicuous than those of the species, they do add to the pleasing combinations of color which are the distinctive advantage of this plant.

FRUIT

The size, shape and character of berries of 'Cinderella' are virtually indistinguishable from those of the species with the possible exception that this plant may bear slightly more heavily in terms of numbers of berries.

FOLIAGE

Quantity of foliage within the tree is normal to slightly greater than the species. Leaf texture, shape, and length are typical of *Cornus racemosa.* They hold up extremely well in full sun situations.

While leaf colors do not substantially fade during the summer, leaf color changes with the seasons to develop attractive reddish hues which intensify in the fall. Leaf color on the top surface is near 5 GY chip 4/5 to about 5 GY 6/6, in the central portion, with a predominant marginal portions approaching 10 Y values of about 5/8 to about 9/4.

Leaves are characteristically variegated, having generally a deep green continuous central portion, surrounded by a light yellowish to cream margin of no specific shapes or patterns. These two colors dominate the upper surface of the leaves, and roughly evenly divide the area of the individual leaves. Normally, intermediate the dark green central and marginal yellow patterns, and intermediate green coloration may be expressed in random blotches due, apparently, to at least one overlying layer of mesophyll cells which is absent chlorophyll to mask the chlorophyll coloration in at least one layer of normal chlorophyll content. Each color occurs in no distinct pattern and is characterized by its random and haphazard pattern. Leaf petioles contain purple hued pigments which fade increasingly with distance from the petiolar attachment along the midrib of the leaf, and normally, disappears before about the fourth major leaf vein, counting from the petiolar attachment. Leaf margins are entire, with slight undulations. Leaves are slightly to moderately cupped in cross-section, and have glossy top surfaces, and have slightly less glossy undersurfaces which have scant to no hairs. Leaf bottom surfaces show generally the same color patterns as the top surfaces.

I claim:

1. A new and distinct variety of Grey Dogwood plant substantially as herein shown and described, being a sport of 'Heaven Sent' and characterized particularly as to novelty by the unique combination of vigorous, disease free growth under good growing conditions, with distinctive variegated foliage having a dark green center, medium green intermediate blotches and yellow to cream margins when mature; the variegated leaves revealing a more vivid autumn coloration than the species; and, the exceptional winter hardiness of this plant extends the ornamental plant selection into areas previously denied.

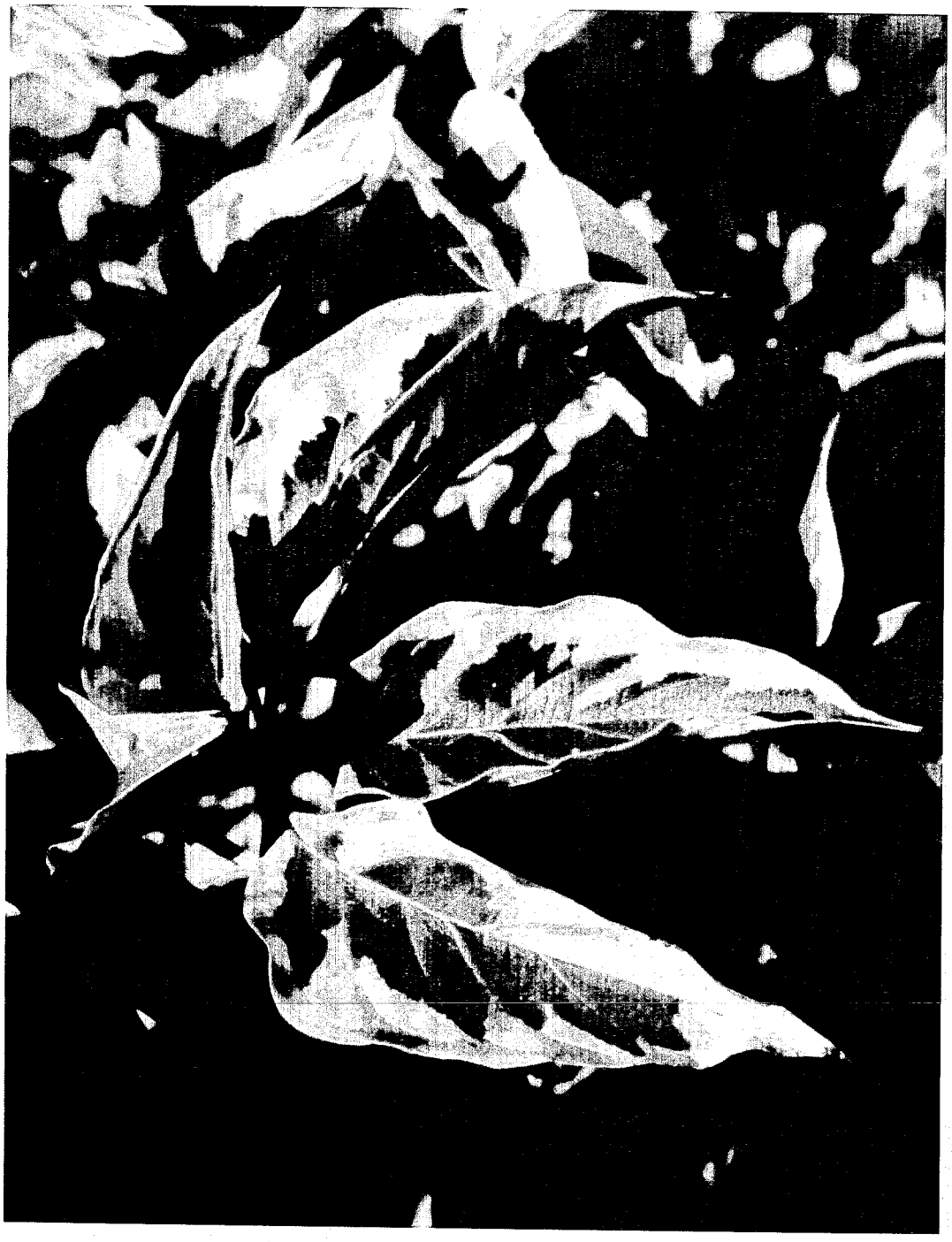

* * * * *